US00PP23209P2

(12) United States Plant Patent
Trucks

(10) Patent No.: US PP23,209 P2
(45) Date of Patent: Nov. 20, 2012

(54) ***PANICUM* PLANT NAMED 'CHEYENNE SKY'**

(50) Latin Name: *Panicum virgatum*
Varietal Denomination: Cheyenne Sky

(76) Inventor: Gary M Trucks, Benton Harbor, MI (US)

( * ) Notice: Subject to any disclaimer, the term of this patent is extended or adjusted under 35 U.S.C. 154(b) by 578 days.

(21) Appl. No.: 12/583,605

(22) Filed: Aug. 24, 2009

(51) Int. Cl.
*A01H 5/00* (2006.01)

(52) U.S. Cl. ..... Plt./384

(58) Field of Classification Search ..... Plt./384
See application file for complete search history.

(56) References Cited

U.S. PATENT DOCUMENTS

PP17,944 P3 * 8/2007 Brand ..... Plt./384
PP19,367 P2 * 10/2008 Trucks ..... Plt./384

OTHER PUBLICATIONS

Anonymous. "*Panicum virgatum* 'Cheyenne Sky' PPAF" available at http://www.perennialresource.com/plants/ornamental-grasses-sedges-rushes/1764_panicu accessed Mar. 24, 2011.*

* cited by examiner

*Primary Examiner* — Wendy C Haas

(57) ABSTRACT

The new and distinct cultivar of ornamental grass named *Panicum virgatum* 'Cheyenne Sky' with compact habit, erect culms and foliage and becoming concord-grape colored, suitable as a potted plant, for multi-seasonal interest mass or specimen landscaping, and for cut flower arrangements.

1 Drawing Sheet

Botanical classification: *Panicum virgatum.*
Variety denomination: 'Cheyenne Sky'.

BACKGROUND OF THE PLANT

*Panicum virgatum* 'Cheyenne Sky', hereinafter also referred to as 'Cheyenne Sky' and the "new plant" is a new and distinct cultivar of Switch Grass. It was crossed by Gary M. Trucks in the summer of 2002 between *Panicum virgatum* 'Rostrahlbush' (not patented)×*Panicum virgatum* 'Amber Wave' (not patented) at a nursery in Benton Harbor, Mich. and selected for further observation in the summer of 2003.

SUMMARY OF THE PLANT

The plant has been successfully propagated by division at the same perennial plant nursery in Benton Harbor, Mich. and found to produce identical plants that maintain the unique characteristics of the original plant. The plant is stable and reproduces true to type in successive generations of asexual reproduction.

'Cheyenne Sky' differs from its parents as well as all other *Panicum* known to the applicant, in that the plant develops concord-purple colored foliage, that is very upright. The new plant is shorter than 'Amber Wave' and slightly taller than 'Rostralbush', but more upright than both cultivars. The most similar known Switch Grass cultivars are 'RR1' U.S. Plant Pat. No. 17,944 (more commonly know as *Panicum* 'Ruby Ribbons') and 'Prairie Fire' U.S Plant Pat. No. 19,367. In comparison to 'Ruby Ribbons' the new plant is taller, more upright in foliage habit and develops less red and more purple in the foliage. In comparison to 'Prairie Fire' the new plant is shorter, more upright in foliage, and with less gray mixed with purple in the foliage.

Comparison Table

| CULTIVAR | HEIGHT (cm) | INITIAL COLOR | SEASONAL COLOR | SEASON OF CHANGE | HABIT |
|---|---|---|---|---|---|
| 'Cheyenne Sky' | 112 | Blue green | Concord purple | Early July | Very Upright |
| 'Haense Herms' (not patented) | 100 | Green | Red purple | Early August | Upright |
| 'Prairie Fire' | 100 | Blue green | Grayed purple | Early July | Upright Upright |
| 'Rostrahlbush' (not patented) | 110 | Green | Red purple | Early August | Upright |
| 'Ruby Ribbons' PP | 55 | Blue green | Red purple | Mid July | Upright |
| 'Shenandoah' (not patented) | 140 | Blue green | Red purple | Late July | arching |

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

GENERAL DESCRIPTION OF THE PLANT

Figure 1:
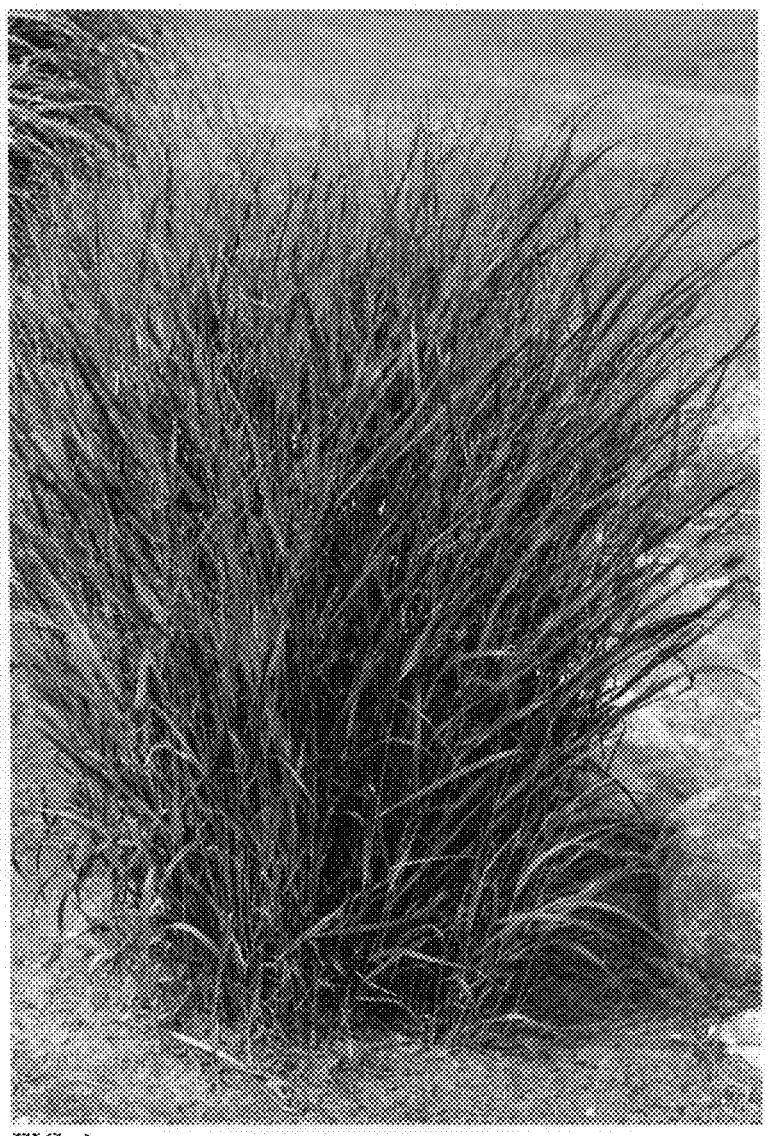
FIG. 1 shows the overall plant in mid-season.
Figure 2:
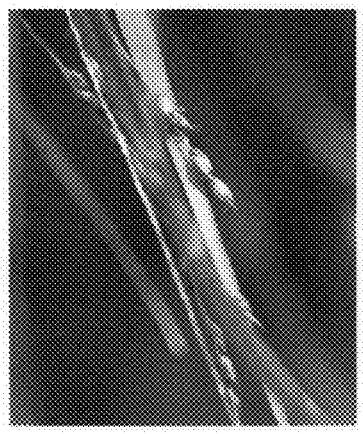
FIG. 2 shows a close-up of the inflorescence in early to mid-August.

*Panicum virgatum* is native to all but the Pacific Coast states of the Mainland United States in addition to parts of Canada and Central America. There are several selected cultivars in production or commerce. *Panicum virgatum* 'Cheyenne Sky' differs from all of these known to the inventor in that it has:

1. Blue green foliage that develops early in the season to a concord purple.
2. Short compact habit with foliage very upright allowing coloration to occur on both sides of foliage.

DETAILED BOTANICAL DESCRIPTION

The following descriptions and color references are based on the 2001 edition of The Royal Horticultural Society Colour Chart except where common dictionary terms are used. The new plant, 'Cheyenne Sky', has not been observed under all possible environments. The phenotype may vary slightly with different environmental conditions, such as temperature, light, fertility, moisture and maturity levels, but without any change in the genotype. The following observations and size descriptions are of a four-year old plant in a trial garden in Benton Harbor, Mich. in full sun with supplemental water and fertilizer.

Parentage: Controlled cross of *Panicum virgatum* 'Rostrahlbush' (female)×*Panicum virgatum* 'Amber Wave' (male).

Propagation:

*Method*.—By division of the culms; Time to finishing in a 3.8 liter pot: three months; Rooting habit: normal, coarsely branching.

Plant description:

*Plant shape and habit*.—Hardy herbaceous perennial forming tightly rhizomatous clump, with very upright culms topped with finely textured airy inflorescence producing a narrow clump taller than wide.

*Plant size*.—Foliage height at flowering is about 112 cm tall from soil line to the top of the foliage; about 45 cm wide at soil line and about 90 to 95 cm at widest point at the flowers.

Foliage description: Glabrous, with microscopic marginal dentations, flat, alternate along culm, erect through tips, sheathed from node of attachment to ligule, linear, deciduous but persist through winter.

*Foliage size*.—25 to 32 cm long, shorter at distal end, averaging 30 cm; 8 to 10 mm wide, averaging 9 mm.

*Foliage color*.—Adaxial surface early season and young foliage: RHS 137A; Abaxial surface early season and young foliage: closest to RHS 138A; Adaxial surface mid season and later: nearest RHS N186B; Abaxial surface mid season and later: mixtures of RHS 187A and RHS 183A with portions near the culm of RHS N138B.

*Veins*.—Parallel; color same as the surrounding leaf on both the top and bottom of the leaf.

*Culm* (*stem*).—Erect, cylindrical, 75% enclosed by leaf sheath, about seven nodes per culm; about 120 per clump.

*Culm dimension*.—80 to 88 cm long without panicle; including panicle between 105 and 115 cm long with average about 112 cm; about 3.0 mm diameter at base; internode length 15 to 22 cm.

*Culm color*.—Mixture of RHS N186C and RHS 137A with portions 4 mm above node nearest RHS 145C and 3 mm below node nearest RHS 144C.

*Node description*.—About 7 per culm, between 3 to 4 mm diameter and length 4 to 5 mm; closest to RHS 199B where receiving full sun exposure, nearest RHS 199D where less exposed.

Flower description: Finely branched open panicle, one panicle per culm.

*Flower timing*.—Beginning early August, flowering through late August and panicles dry and remain effective through winter; No fragrance detected.

*Panicle*.—Pyramidal, about 30 cm long and 25 cm wide; overall effective color RHS 187A.

*Rachis*.—Branched, about 30 cm long and 1 mm at base; starting RHS N138C and coloring up to RHS N187A.

*Pedicel*.—Thin, cylindrical, between 2 cm and 5 cm long and less than 1 mm diameter, starting RHS N138C and coloring up to RHS N187A.

*Rachilla*.—Thin, about 5 mm long and 0.2 mm diameter; color starting RHS 137D and developing to RHS N187A.

*Lower glume*.—About 2.5 mm long and 1 mm wide; nearest RHS 187B.

*Lemma*.—Outer and inner — both about 3 mm long and 1.5 mm wide, and RHS 187B on surfaces exposed to sun, RHS 145A in areas minimally exposed to sun and RHS 157C areas protected from sun.

*Spikelet*.—Usually with 2 flowers, 1.5 to 2.5 cm long and 2.5 mm wide.

*Gynoecium*.—Stigma — two, feathered, protruding 1 to 2 mm from glume, RHS 59A.

*Androecium*.—Filaments — fine, hair-like, white, less than 0.1 mm diameter and up to 2.0 mm long, joined near longitudinal middle of anther; Anthers: two 2.0 to 3.0 mm long, 1.0 mm wide, nearest RHS N25A.

*Pollen*.—Round, less than 0.1 mm in diameter, nearly transparent lighter than RHS 155D.

*Fruit*.—Caryopsis; 2 to 3 mm long and 1.5 mm wide, nearest RHS 164C.

Hardiness, pest and disease resistance: The plant grows best with plenty of moisture and adequate drainage, but is able to tolerate some drought when mature. Hardiness at least from USDA zone 4 through 9. Disease and pest resistance beyond what is typical of that of other Switch Grasses has not been observed.

I claim:

1. A new and distinct cultivar of ornamental grass plant, *Panicum virgatum* 'Cheyenne Sky' as herein described and illustrated, with compact habit, erect culms and foliage and becoming concord-grape colored, suitable as a potted plant, for multi-seasonal garden interest, and for cut flower arrangements.

* * * * *